(12) United States Patent
Bystryak et al.

(10) Patent No.: US 7,989,177 B2
(45) Date of Patent: Aug. 2, 2011

(54) METHOD AND DEVICE FOR ULTRASOUND ASSISTED PARTICLE AGGLUTINATION ASSAY

(75) Inventors: Simon Bystryak, Budd Lake, NJ (US); Natalya Ossina, Princeton, NJ (US); Armen P. Sarvazyan, Lambertville, NJ (US)

(73) Assignee: Allied Innovative Systems, LLC, Budd Lake, NJ (US)

( * ) Notice: Subject to any disclaimer, the term of this patent is extended or adjusted under 35 U.S.C. 154(b) by 1007 days.

(21) Appl. No.: 11/846,551

(22) Filed: Aug. 29, 2007

(65) Prior Publication Data

US 2009/0053688 A1 Feb. 26, 2009

Related U.S. Application Data

(63) Continuation-in-part of application No. 11/841,456, filed on Aug. 20, 2007, now abandoned.

(51) Int. Cl.
*G01N 33/00* (2006.01)
(52) U.S. Cl. ............... 435/7.92; 435/4; 435/5; 435/174; 436/523; 436/524
(58) Field of Classification Search .................. None
See application file for complete search history.

(56) References Cited

U.S. PATENT DOCUMENTS

| | | | | |
|---|---|---|---|---|
| 4,759,775 A | * | 7/1988 | Peterson et al. | 210/708 |
| 5,665,605 A | * | 9/1997 | Coakley et al. | 436/174 |
| 5,853,994 A | * | 12/1998 | Gopinathan et al. | 435/6 |
| 5,912,182 A | | 6/1999 | Coakley | |

* cited by examiner

*Primary Examiner* — N. C. Yang
(74) *Attorney, Agent, or Firm* — Boris Leschinsky (57) ABSTRACT

Ultrasound-assisted particle agglutination assay methods and apparatuses are described based on first providing a standing wave ultrasound field at a resonance frequency of a test liquid in a resonator cell containing microparticles covered with a binding agent with high affinity to an analyte sought to be detected by the assay test. Formation of the specifically-bound and nonspecifically-bound aggregates of these microparticles is then followed by effective stirring of the liquid with swept-frequency sonication causing disintegration of nonspecifically-bound aggregates and leaving specifically-bound aggregates in place for further detection and measurement. The methods and devices of the invention allow significant improvement in the sensitivity and specificity of agglutination tests and are advantageously applicable to detecting various proteins, DNA, RNA and other biologically active substances. Specific examples are provided.

23 Claims, 9 Drawing Sheets

METHOD AND DEVICE FOR ULTRASOUND ASSISTED PARTICLE AGGLUTINATION ASSAY

CROSS REFERENCE TO A RELATED APPLICATION

This application is a continuation-in-part of a co-pending U.S. patent application Ser. No. 11/841,456, entitled "Ultrasonic stirring of liquids in small volumes" filed on Aug. 20, 2007, which is hereby incorporated in its entirety by reference.

FIELD OF THE INVENTION

The present invention relates to a method and apparatus for ultrasound-assisted agglutination assays based on the formation of aggregates of microparticles in the presence of an analyte in the sample. More specifically, the invention relates to the use of the swept-frequency mode of ultrasound treatment to improve the sensitivity of the bead and red cell-based immunoassays, such as the latex agglutination and haemagglutination tests used for identification and quantification of analytes of different origins: proteins, DNA, RNA, physiologically active substances, and other biomolecules and substances of biological importance.

BACKGROUND OF THE INVENTION

Immunoassay-based techniques for identification and quantification of various analytes and specifically particle agglutination immunoassays are widely used in medicine, pharmacology and food industry. There are several ways to conduct particle agglutination assays and to detect positive agglutination reactions. Conventional agglutination tests are based on the formation of aggregates of colloidal particles in the presence of an analyte in the sample. Agglutinated heavy aggregates can be revealed by the naked eye or by expensive equipment, such as spectrophotometers, nephelometers, scanning laser microscopy, magnetic moment analysis, photon correlation spectroscopy and fluorescence analysis, and other instruments that measure transmitted, absorbed, or scattered light. Although, these instrumental methods have now been applied to a wide variety of commercial assays, they are not considered simple rapid tests because expensive instrumentation is required.

Particle agglutination assays can be performed either in a microtiter plate or on hydrophobic agglutination slides. The slide is usually kept rotated for several minutes and agglutination of latex particles is recorded visually while rotating the slide.

The detection of the agglutination reaction by the naked eye is a subjective procedure. Particle agglutination results vary from one clinical laboratory to another and reported results obtained with the same serum may vary even between technicians in the same laboratory. This situation makes it difficult for the physician to interpret reported results. Indeed, in some medical centers, physicians will request that the same technician perform all HIV antibody testing and blood typing to maintain consistency. This poses problems for the physician when the technician leaves or the physician moves to a new hospital or to another city. In other laboratories, several technicians interpret the same results independently. On the whole, because of the subjective interpretation of the results, the particle agglutination assays may suffer from higher numbers of false positives and false negatives. This situation affects significantly the performance (clinical sensitivity and specificity) of the assay.

There are mainly three serious drawbacks of the conventional particle agglutination methods: 1) a long analysis time; hence, the need for mechanical rotational motion of microtiter plates or agglutination slides to accelerate the agglutination process, 2) a limited analytical sensitivity of the assay, and 3) difficulty and subjectivity in interpretation of the assay results. In order to circumvent these drawbacks of agglutination assays, a number of approaches have been developed.

In particular, it has been shown that the detection rate and sensitivity of coated particle agglutination immunoassays are increased in ultrasonic standing waves (Wiklund M, Hertz H M. Ultrasonic enhancement of bead-based bioaffinity assays. Lab Chip. 2006 October; 6(10):1279-92). U.S. Pat. Nos. 5,665,605 and 5,912,182 issued to Coakley et al. and incorporated herein by reference in their entirety, disclose a particle agglutination method based on the use of ultrasound to enhance the agglutination process; specifically, to shorten the time of analysis and to increase the sensitivity of the assay.

As known in the prior art, when particles suspended in a fluid are subjected to an ultrasonic standing wave field of a particular single frequency, the particles displace to the locations of the standing wave nodes. The concentration of particles in the standing wave field increases the rate of particle agglutination and the sensitivity of antigen detection. The rate is increased because the local concentration of beads is accentuated in a standing wave field.

As a result of applying a standing wave field to the resonator cell, microparticles are clumped together in one of two ways. In the first, specifically-bound agglutinated microparticles form a strong immunochemical or another specific bond in an aggregate. The second type of aggregates is in the form of clumps of nonspecifically-bound microparticles that are attached to each other by various weak forces.

Despite the significant improvement of the particle agglutination tests due to application of ultrasonic standing waves, this approach suffers from the same drawback as other particle agglutination-based methods: significant error due to the presence of both specifically-bound and nonspecifically-bound aggregates. A solution to this problem could be provided by efficient microstirring capable of destroying these nonspecifically-bound aggregates.

Stirring liquids is a necessary part of many industrial, chemical and pharmaceutical processes, and there are many conventional stirring methods developed for these industrial processes. Since most of these processes are carried out on macroscopic scales, the stirring methods with various conventional mechanically or magnetically driven stirring elements are not applicable to small volume samples used in agglutination immunoassays. It has only been in the recent years that stirring of small quantities of liquids has become technologically relevant in the context of microfluidics, since stirring and mixing are often crucial to the effective functioning of devices manipulating with small quantities of liquids. (Nguyen, N. & Werely, S. 2002 Fundamentals and applications of microfluidics. Boston, Mass.).

Numerous methods of stirring in microvolumes of liquid have been developed. These methods can be categorized to be of two types: with and without moving parts. The moving parts stirrers include microscopic stirrer bars, piezoelectric membranes or oscillating gas bubbles. The mixing can also be achieved without moving parts by action of electrical or acoustic fields on the liquid. U.S. Pat. No. 7,081,189 issued to Squires et al. discloses microfluidic stirrer and mixer driven by induced-charge electro-osmosis applied to electrolyte fluids. Liu et al. developed an approach to microstirring based on acoustic microstreaming around an array of small air bubbles resting at the bottom of the test chamber (Liu, R., Lenigk, R., Druyor-Sanchez, R. L., Yang, J. & Grodzinski, P. 2003 Hybridization enhancement using cavitation microstreaming. Analyt. Chem. 75, 1911-1917). When bubbles are vibrated by a sound field, they create steady circular microflows around them. U.S. Pat. No. 6,244,738 issued to Yasuda et al. discloses ultrasonic vibrators arranged in the stirring tube where several sample solutions are stirred and mixed by an acoustic streaming induced by ultrasonic vibration.

Applicability of these microstirring methods to ultrasound-assisted particle agglutination tests for destroying nonspecifically bound aggregates and increasing the sensitivity of the tests is highly limited. It is difficult to use known stirring techniques without significant modification of the particle agglutination technology. Thus, there is a need for a method and device that would not only preserve all advantages of ultrasound standing wave-assisted particle agglutination technology but also provide efficient microstirring aimed to destroy nonspecifically-bound aggregates, therefore improving signal-to-noise ratio in quantitative assessment of the amount of immunochemically-bound aggregates.

SUMMARY OF THE INVENTION

In accordance with this invention, there is provided a method and apparatus for sensitive detection, identification and quantification of various analytes including proteins, DNA, RNA, and other biomolecules and substances of biological importance using ultrasound-assisted particle agglutination test, in which two phases of ultrasound treatment are employed. In the first, sonication by at least one standing ultrasonic wave is applied to drive them to locations of nodal pattern characterized by potential energy minima conditions. That in turn forms particle clusters and accelerates particle aggregation process forming specifically- and nonspecifically-bound aggregates of microparticles. In a second phase, swept-frequency sonication is applied aiming at effective stirring of the sample and disintegration of nonspecifically-bound aggregates. Such disintegration is aimed at leaving only specifically-bound aggregates in the liquid and, therefore, provides for much more accurate assessment of the presence and quantity of these specifically-bonded aggregates and, consequently, more sensitive detection of target agents. The term immunochemically-bonded aggregate refers to one type of specifically-bonded aggregate as immunochemical bonds are one of the strongest specific bonds forming such aggregates.

The method of the invention is based on collecting microparticles in the nodes or antinodes (depending on density and compressibility of the particle material) of the standing waves generated in an acoustic resonator cell. In the swept-frequency mode of sonication, a driving frequency of the ultrasound transducer is varied from a predetermined minimum frequency to a predetermined maximum frequency. The range is selected to include at least two resonance frequencies of the liquid on the resonator cell. Every time when the ratio of the resonator characteristic dimension becomes close to the whole number of the acoustic half-wavelengths, a standing wave is formed in the resonator cell and the microparticles suspended in the liquid are urged to move to locations of the nodal pattern defined by the frequency of the standing wave. Sweeping of the frequency results in continuous changes of the ultrasound wavelengths and, consequently, in the appearance and disappearance of standing waves at various resonance frequencies. That in turn causes repeated appearance and subsequent disappearance of the corresponding nodal patterns (at least two resonance frequencies of the liquid in the resonator cell are included in the frequency sweep range) at various locations throughout the resonator cell. This further results in the continuous assembling and disassembling of microparticle bands, that is, in continuous jumping of the microparticles from one location to another.

Frequency sweeping acts, as a highly efficient stirrer: millions of micron size particles are moving with velocities on the order of 100 mm/s relative to surrounding fluid. Movements of nonspecifically-bound aggregates around the resonator cell from one location to another cause their break-up. At the same time, specifically-bound aggregates can easily withstand such movements without splitting up. After one or preferably several cycles of frequency sweeping, nonspecifically-bound aggregates are disintegrated, and their amount decreases significantly whereas specifically bound aggregates remain intact. Thus in the first phase, the standing wave ultrasonic treatment of the sample results in acceleration of the agglutination process. In the second phase, switching to the swept-frequency mode of ultrasonic exposure leads to significant decrease in the background ("noise") caused by the presence of nonspecifically-bound aggregates. On the whole, the use of sequential standing wave and swept-frequency modes of ultrasonic treatment results in significant increase of signal-to-noise ratio. The amount of aggregates left in the liquid are then evaluated by any known aggregate detection means including, for example, acoustical or optical means.

The term "microparticles" refers to particles of different origin including but not limited to latex beads, glass and silica microparticles, clay minerals, proteins and biological cells. They are typically coated or otherwise covered with an appropriate binding agent having high affinity to a particular analyte, the presence of which is sought to be determined by a particular assay.

Also in accordance with the present invention, there is provided an apparatus for sensitive detection, identification and quantification of various analytes, proteins, DNA, RNA, and other biomolecules and substances of biological importance based on immunoprecipitation of antigen-antibodies complexes that are bound to the microparticles. The apparatus includes at least one ultrasonic resonator cell adapted to first accelerate immunochemical reactions, then disintegrate nonspecifically-bound aggregates of microparticles and, finally, to provide the quantitative assessment of specifically-bound aggregates by ultrasound scattering measurements.

According to one aspect of the present invention, the assessment of the microparticles aggregates is conducted using optical aggregate detection means by visualizing and analyzing the patterns of the aggregated microparticles in the resonator cell.

According to another aspect of the invention, the resonator cell could be formed by two plane-parallel surfaces that have high acoustic reflectivity. In one exemplary design of the invention, the resonator cell can be made in the form of a tube, in which cylindrical standing waves can be generated. In another exemplary design of the invention, the resonator cell can be of any arbitrary shape, which allows generation of several modes of acoustic standing waves.

The preferred frequency range employed for sweep-frequency mode of sonication in the microparticle agglutination tests is about 1-50 MHz, which corresponds to the range of acoustic wavelengths in the aqueous solutions from about 1,500 micrometer to about 30 micrometer. This range is defined by several factors. One factor is the level of difficulty associated to rapid move the microparticles from one nodal position to another if the distance between these nodes is more than 1 mm. Another factor is that in the applications of the method of present invention, characteristic dimensions of the resonator cell containing the test liquid is typically in the range from 1 mm to 5 mm. Yet another factor is that at high frequencies, attenuation of ultrasound is greatly increased and there may not be enough intensity of a reflected wave to generate standing waves (the attenuation in water and in aqueous solution is approximately proportional to the square of the ultrasound frequency). Yet another factor is that in order to obtain a standing wave in the liquid, the dimensions of the vessel containing that liquid should be from a few to tens of half-wavelengths of ultrasound.

The method and apparatus of the invention have a great potential to meet the needs for sensitive, selective, simple, easy to operate and cost-effective assays that can be easily implemented at clinics and laboratories for routine diagnosis of various diseases. The method of the invention could be easily adapted to detect any target molecules, microorganisms and viruses for which antibodies can be raised. But despite the common basis of the technology, most of the parameters for conducting the assay using the method of the current invention must be thoroughly optimized for each system. Depending on dimensions and acoustical properties of microparticles, optimal operating frequencies, intensities and time of ultrasonic exposure, number of cycles and rate of frequency change for swept-frequency stirring, etc., could be different for different agglutination assays.

In certain applications, the method of the invention can be implemented using only the swept-frequency mode of sonication, without preliminary treatment at a fixed frequency standing wave sonication. The short periods of generation of various harmonics of standing waves during swept-frequency mode of sonication may be sufficient by themselves for both accelerating the immunochemical reaction in the first phase and disintegrating nonspecifically-bonded aggregates in the second phase. The swept-frequency sonication may be performed either by continuous (with fixed or variable rate of changing the frequency) or stepwise sweeping the frequency of ultrasound. In certain applications of the method of the invention, it might be optimal to use such stepwise sweeping the frequency, where the system discretely "jumps" from one harmonic of standing waves to another. Other variations of the method include conducting the first pass of the swept-frequency sonication at a slow rate so that enough time is allowed to complete the first phase (acceleration of specific reaction) of the process. Following repetitions of the swept-frequency sonication may be done at a faster rate of frequency change to ensure effective stirring of the liquid.

Specific examples of potential applications of ultrasound-assisted agglutination method of the invention include but not limited to:
- testing of infectious diseases, such as malaria, tuberculosis, West Nile virus, HIV and bio-terror agents; as wells as newly emerging pathogens of severe acute respiratory syndrome-associated coronavirus (SARS-CoV), henipaviruses (Hendra and Nipah), and, most recently, avian influenza viruses that have caused illness and deaths in humans with the threat of evolving into a pandemic;
- blood group testing based on haemagglutination and latex agglutination assays;
- cardiac biomarker testing, for example, for the management of Acute Coronary Syndromes (ACS);
- food-borne and water-borne pathogenic bacteria testing, such as *E. coli, Salmonella, Listeria, Campylobacter* and other.

BRIEF DESCRIPTION OF THE DRAWINGS

Embodiments of this invention will now be described by way of examples only and with reference to the accompanying drawings, in which.

DESCRIPTION OF THE PREFERRED EMBODIMENTS OF THE INVENTION

In various figures, the same references designate identical or similar elements.

Figure 1:
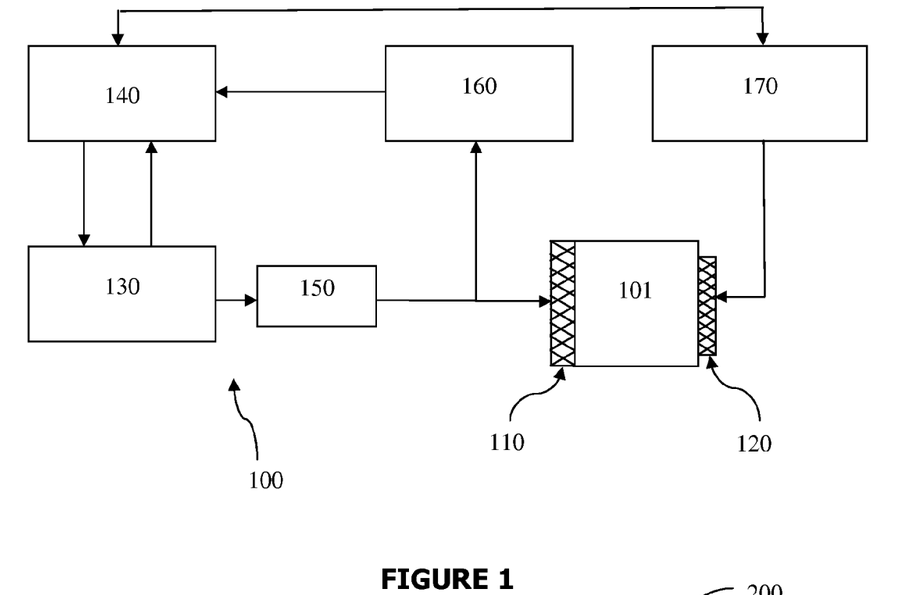
FIG. 1 presents a block-diagram of the device according to the first embodiment of the invention.

Referring to FIG. 1, there is shown a block-diagram of the device 100 according to the first embodiment of the invention. The device includes a resonator cell 101 filled with microparticle agglutination assay mixture composed of a tested liquid and a suspension of microparticles with attached binding agent, such as an antibody to a target analyte. A stirring transducer 110 generates ultrasonic standing waves in the liquid filling the resonator cell 101. The frequency range for ultrasonic standing wave in the resonator cell 101 is typically 1-50 MHz. The resonator cell 101 can be formed by the surface of the stirring transducer 110 and a plane-parallel reflector located opposite to the stirring transducer 110 so that ultrasonic wave may travel back and forth forming standing waves at certain frequencies of excitation signal. The ultrasound transducers used for the purposes of this invention typically come in the form of a disc, plate or a film made of piezoceramics, piezopolymer, or other material that can generate acoustic waves under alternating current (a.c.) excitation. The resonator cell 101 could be also formed by a vessel of arbitrary shape as soon as its walls provide effective reflection of acoustic waves, creating at certain frequencies the nodes of standing waves at various locations of the vessel. Microparticles suspended in the liquid filling the resonator cell, when subjected to an acoustic standing wave field, are displaced to the locations of the standing wave nodal pattern. Sweeping the frequency of the a.c. signal driving the transducer results in successive appearance of many nodal patterns of standing waves and therefore in repetitive changing in the locations of standing wave nodes. Correspondingly, the suspended microparticles are dragged from one location of the nodes to another, acting as effective microstirrer of the liquid.

Transducer excitation a.c. signal is generated by a voltage controlled oscillator (VCO) 130. A microprocessor 140 is used to generate a sweep of voltage, which is sent out to VCO 130. Corresponding to the voltage sweep, the VCO 130 provides a sweep of frequency of the a.c. signal. The output of the VCO 130 is sent to the stirring transducer 110 of the resonator cell 101 via a complex resistor 150. The complex resistor 150 acts as a voltage divider and splits the signal proportionally so that it could be utilized for detecting changes of the impedance of the stirring transducer 110 being mechanically loaded by the ultrasonic resonator cell 101. Changes of the stirring transducer impedance detected by the amplitude detector 160 provide a feedback signal to the microprocessor 140 indicating appearance of standing wave at certain resonance frequencies. A particular set of detected resonance frequency values along the sweep obtained by the microprocessor 140 during the initial sweep is of prime importance to the method of current invention. Depending on the type and size of particles, the microprocessor 140 can use different programs and algorithms for continuous or stepwise frequency sweep utilizing information on particular resonance frequencies at which standing waves are formed.

A measuring ultrasonic transducer 120 is attached to the resonator cell 101 and used for quantitative assessment of the amount of specifically-bound aggregates by measuring backscattering properties of the liquid in the resonator cell 101. The measuring transducer 120 is connected to an electronic pulse-echo system 170, which transmits and receives short ultrasonic pulses, working therefore in the pulse-echo ultrasonic mode. Electronic system 170 acts as an aggregate detection means together with the transducer 120. It is connected to the microprocessor 140, which triggers the beginning of the measurement of ultrasound backscattering in the sample. The frequency range for the backscattering measurement is preferably 50-150 Mhz.

The forces responsible for redistributing particles in the liquid in accordance with the standing field pattern depend on the relative density and acoustic impedance of the particles with respect to the fluid in which they are suspended, the dimensions of the particles and the frequency of the standing ultrasonic wave. Ultrasound radiation forces urge the particles to the local particle potential energy minima locations within the pressure nodal planes, to give rise to concentration regions that appear as clumps striated at half-wavelength separation.

The exact information about resonance frequencies of the liquid filled resonator cell 101 may not be available at the beginning of operation of the device since these frequencies are defined by the speed of sound in the liquid filling the resonator cell. This speed depends on the composition and temperature of the liquid filling the resonator cell and these parameters can vary from experiment to experiment. Therefore the control system is designed to be capable of automatic detection of these resonance frequencies by measuring changes of electrical impedance of the stirring transducer 110. When a standing wave is established in the liquid filling the resonator cell 101, the acoustical loading of the stirring transducer 110 changes, thus affecting its electrical impedance. Every time when the driving frequency of the stirring transducer 110 is approaching the resonance frequency of the liquid-filled resonator cell 101, the amplitude and the phase of the signal at the output of the complex resistor 150 significantly changes. These changes are detected by the amplitude and/or phase detector 160 and sent back to the microprocessor 140 indicating the appearance of standing waves at certain resonance frequencies.

Figure 2:
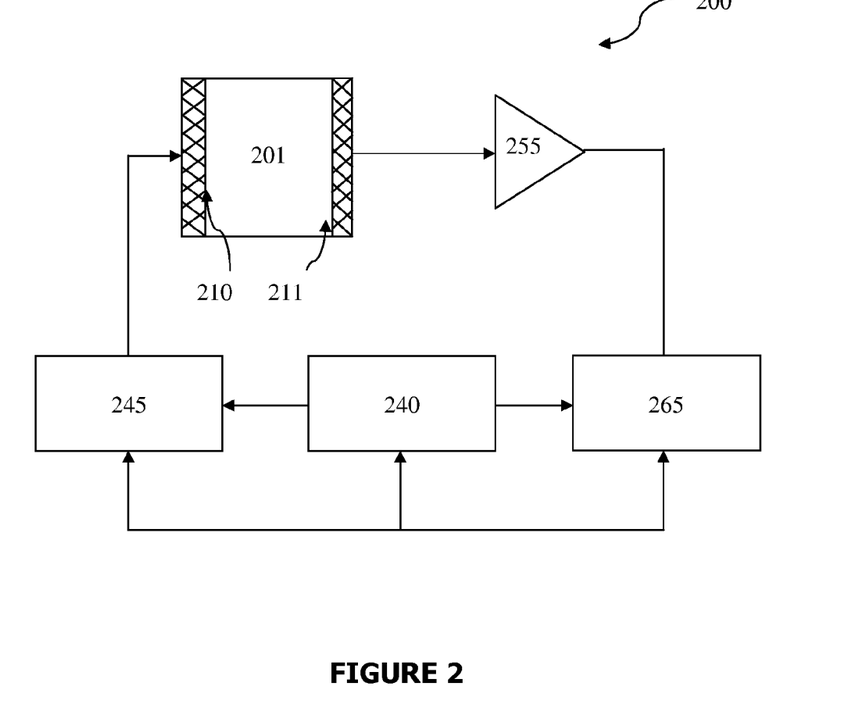
FIG. 2 is a block-diagram of a second embodiment of the device.

FIG. 2 shows a schematic block-diagram of a second embodiment of the invention. In the device 200 according to this embodiment of the invention, an ultrasonic resonator cell 201 is equipped with a stirring ultrasound transducer 210 and a plane-parallel second stirring transducer 211, both transducers being connected to a simple oscillation and feedback circuitry. Operation of the circuit is based on automatically maintaining the standing wave condition characterized by certain phase relationships between transmitted and reflected signals. The phase-locked loop (PLL) 265 automatically maintains the resonance phase relationship between the input and output signals of the resonator cell 201 by changing the oscillation frequency. The circuit maintains the appropriate phase relationship despite variations in temperature or other conditions that alter the sound velocity, and therefore the resonance wavelength in the liquid. The resonator cell 201 functions as the frequency-determining element of the oscillator. Constraining the oscillator to operate in the specific frequency region by adjusting the bandpass of the broadband amplifier 255 allows generating a cylindrical standing wave corresponding to the chosen harmonic of the resonator cell 201. An important feature of the embodiment of the invention is an electronic feedback system, which provides automatic control of the standing wave condition in the vessel independent of variations of temperature. To sweep the frequency, that is to move from one harmonic of the resonance to another, the microprocessor 240 is controlling either the setting of the bandpass filter 245 or the setting of the phase of the PLL circuit 265.

Figure 3:
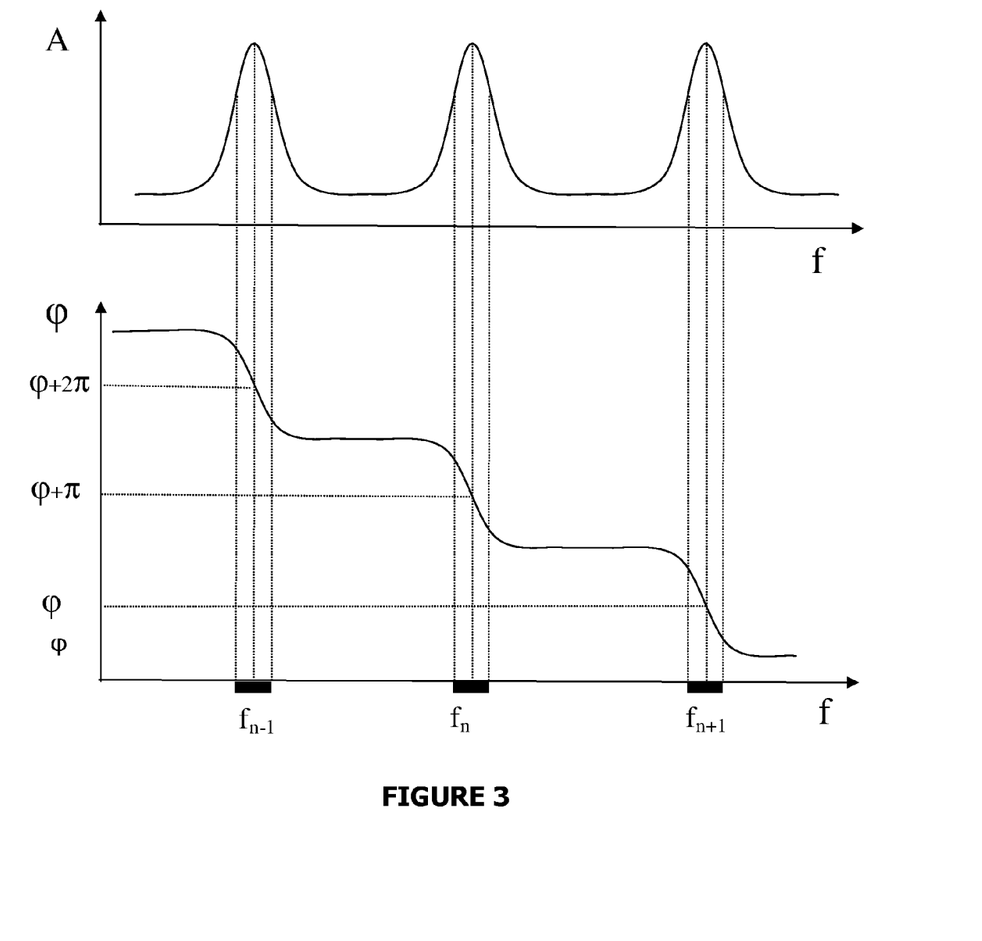
FIG. 3 shows frequency dependences of amplitude and phase of the signal at the output of the resonator of FIG. 2.

The mechanism of switching the standing wave pattern from one harmonic to another and thus changing the position of standing wave nodes is illustrated in FIG. 3. It shows frequency dependences of amplitude and phase of the signal at the output of the resonator of FIG. 2. Standing waves appear in the resonator at the frequency bands $f_{n-1}$, $f_n$, and $f_{n+1}$ marked by bold line on the frequency axis. These marked frequency bands correspond to the amplitude maxima and phase deflection regions as shown in FIG. 3. Switching the system from one resonance to another is provided by the microprocessor 240, which controls setting of the bandpass filter 245 and the PLL chip 265 shown in FIG. 2. There are various modes in which this sweeping frequency can be provided. One is a continuous mode of sweeping frequency, including a sweep at a constant rate of frequency change as well as at a variable rate of frequency change. One useful variation of the variable rate mode is to have a lower rate of frequency change in the vicinity of resonance frequencies therefore allowing for greater time of presence of standing waves. The rate is increased in-between the resonance frequencies such that switching from one nodal pattern to another takes less time.

Another mode swept-frequency sonication is a stepwise changing of sweeping frequency jumping from one resonance frequency band to another. The time of the continuous sweep and/or the temporal parameters of jumping from one resonance frequency to another are those variables that need to be separately optimized for each particular agglutination test.

The control system of the second embodiment may also use measuring control means described for the device in FIG. 1 (not shown on the drawings) or any other measuring control means appropriate for detection of agglutinated aggregates.

Figure 4:
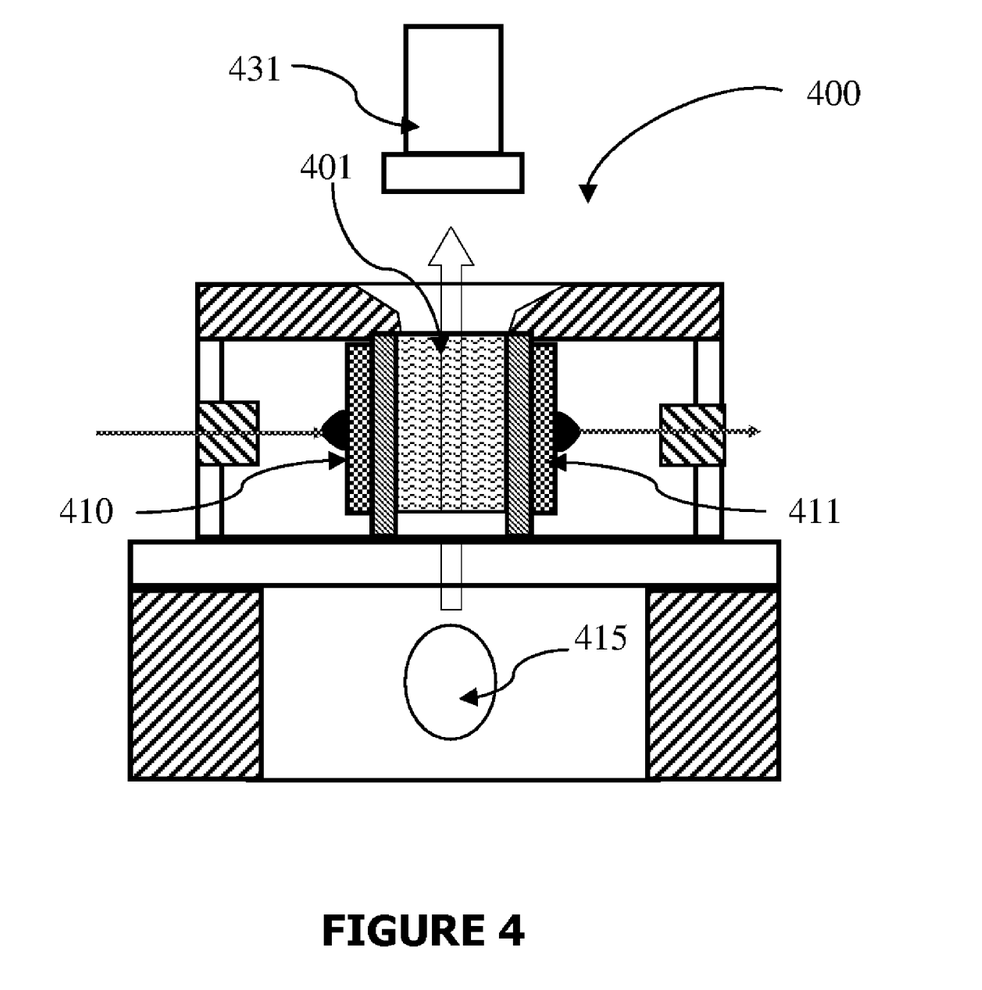
FIG. 4 is a schematic diagram of the measuring cell, similar to that schematically shown on FIG. 2, showing acoustical components and optical part for observing and quantitating particles aggregates.

FIG. 4 shows a cross-sectional view of one particularly useful design of the measuring resonator cell assembly 400 assembled in the device illustrated in FIG. 2 including a resonator cell 401 with stirring ultrasonic transducers 410 and 411 acoustically coupled thereto. Also provided is the optical aggregate detection means 431 adapted for measuring optical properties of the liquid and therefore capable of detection of presence and amount of aggregates of microparticles formed in the process of agglutination. The resonator cell 401 has a transparent bottom allowing illuminating the sample using a light source 415 and an open or transparent top allowing observing the aggregated particles in the standing wave using the optical light detection means 431 such as a microscope equipped with a CCD camera. To make the measurements, the operator only needs to load the reagent mixture into the device, and the quantitative result will be seen on a display in approximately 2-4 minutes. Thus, unlike other particle agglutination methods, subjective evaluation of the test results is eliminated.

The key element of the device is the resonator cell 401, which in the simplest case should consist of two plane and parallel surfaces that have high acoustic reflectivity and that are separated by a multiple of half the acoustic wavelength. Alternatively, the resonator cell 401 can be made of a piezoceramic tube in which cylindrical standing waves can be formed. There are numerous requirements that need to be satisfied to make adequate resonator cells for ultrasound assisted particle agglutination immunoassay device. These requirements are related to both acoustical and optical parameters of the system. In case of using cylindrical standing waves, the geometry of the piezoceramic tube should be such that all major resonances and harmonics of the empty tube are outside the frequency range in which the systems works in both modes: particle aggregation at a fixed frequency in the first phase of the process and swept-frequency mode of sonication during the second phase of the device operation.

The working frequency range for optimal manipulation of particles in the ultrasound standing wave field depends on the diameter of particles. Obviously, optimal conditions for aggregating for example latex particles of 1 micron in diameter and red blood cells, which are about one order of magnitude bigger, will be quite different. The diameter of the cylindrical resonator cell needs to be chosen so that the working volume of the cell is within 4-100 microliter limits, which appears to be optimal for immunoassay application. The height of the cell should be not much different from its diameter to provide easy filling and cleaning the cell. The height should be large enough so that sufficient acoustic energy is delivered into the liquid filling the cell. At the same time, it should be as short as possible to allow accurate optical detection of particle aggregates in the cell. To be able to make optical detection of aggregated particles, the bottom of the cell needs to be made transparent.

One of the factors that may complicate the use of the device is the necessity of careful cleaning of the measuring resonator cell after each experiment to provide reproducible measurement results. Besides, cleaning of the cell is one of the most time-consuming procedures in the device preparation for measurement of each successive sample. Therefore, the use of disposable measuring cells for each experiment is highly desirable. In addition, the use of such cells allows one to avoid contamination of the successive samples and minimize sample handling.

FIGS. 5-8 illustrate a third embodiment of the device in accordance with the invention using at least one disposable resonator cell station. Disposable resonator cells can be made either from a transparent plastic or from a metal with a transparent bottom incorporated therewith, which is needed when optical detection of aggregated particles is used.

Figure 5:
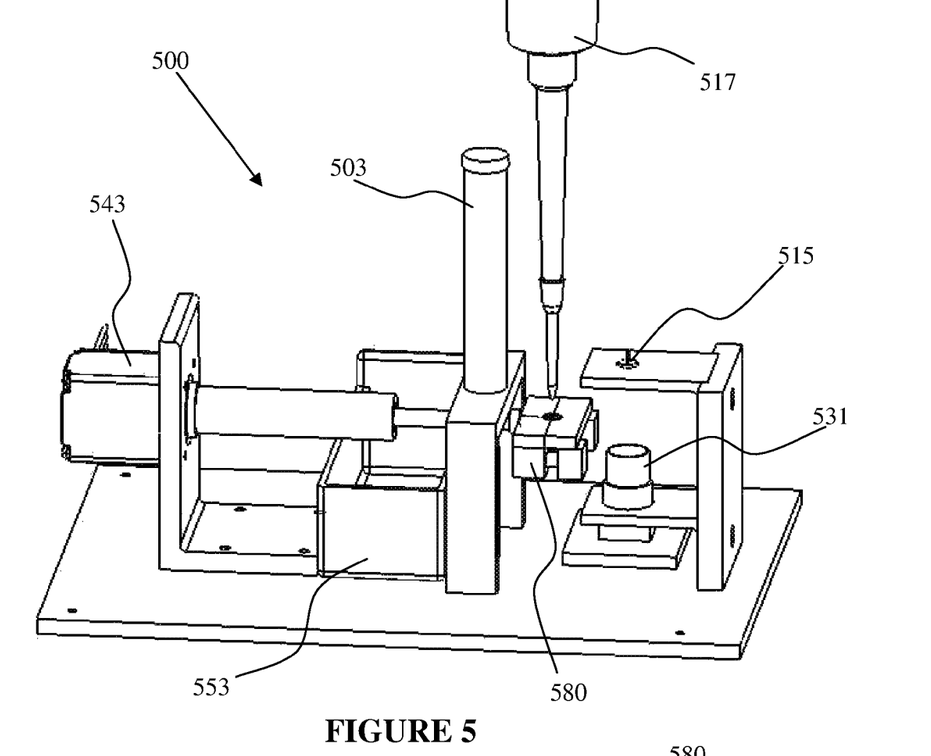
FIG. 5 is an isometric view of a third embodiment of the invention.

The device shown in FIG. 5 includes a resonator cell assembly 580 supported by and moved between one of four positions by a moving means such as a linear actuator 543. These positions are referred to as first through fourth based on the corresponding stage in the process and not based on a geometrical location in the device. The first such position for the resonator cell assembly is at the disposable cell loading station including a cell cartridge 503. Manual or automatic loading of a disposable cell into the cell holder is accomplished here. The second position is at the sample loading station. The third position is at the measuring station and the fourth position is at the cell discarding station.

Figure 6:
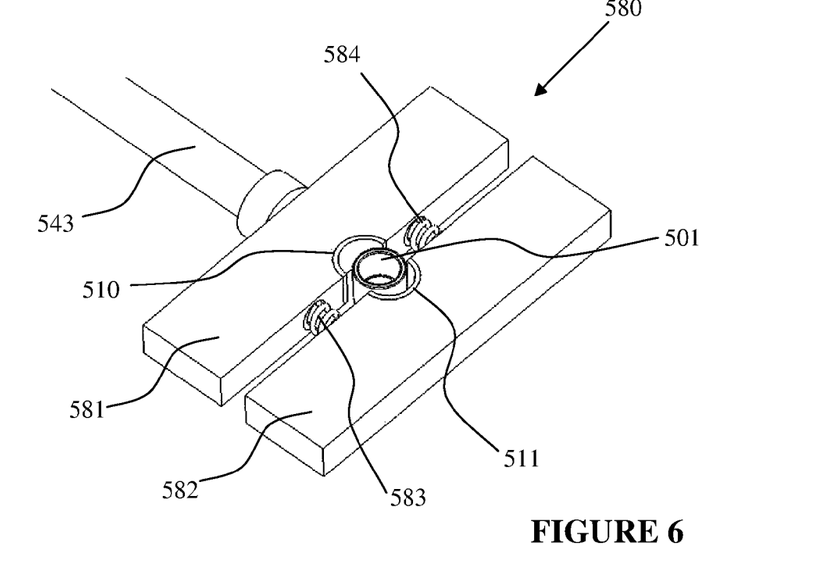
FIG. 6 is an enlarged isometric view of the cylindrical disposable cell inserted in the cell holder assembly comprising two piezotransducers.

FIG. 6 shows an exemplary cylindrical resonator cell 501 placed in the cell assembly 580 between two segments of piezoceramic tube transducers 510 and 511 having their inner diameter equal to the outer diameter of the disposable resonator cell 501. The resonator cell assembly 580 includes a holder comprising a pair of grips 581 and 582 shown in FIG. 6 including features adapted to hold the transducers 510 and 511 and the cell 501 therebetween in a "closed" position of the holder. The grips 581 and 582 are held together by two normally-closed extension springs 583 and 584.

Figure 7:
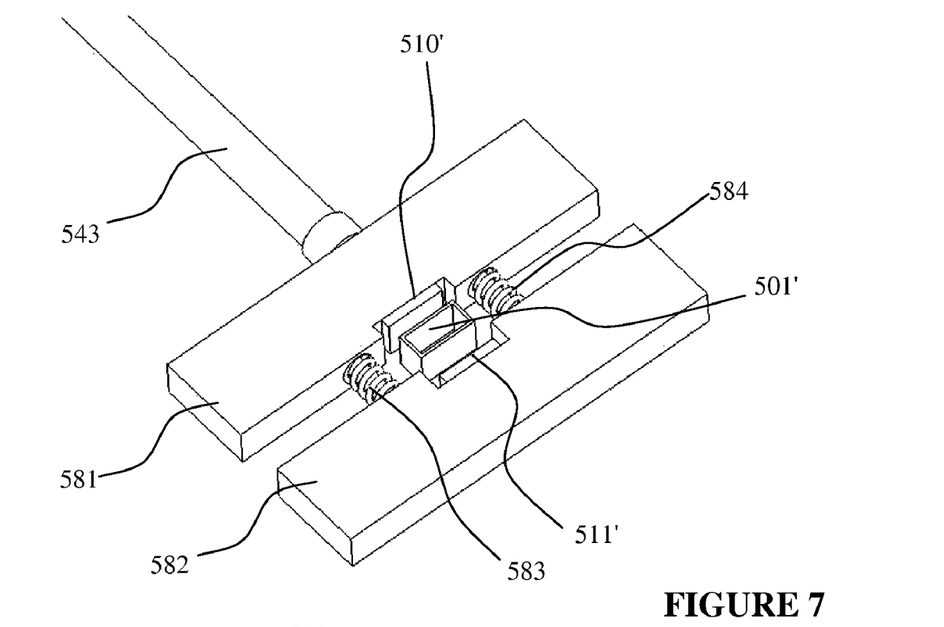
FIG. 7 is an enlarged isometric view of the rectangular disposable cell inserted in the cell holder assembly comprising two piezotransducers.

FIG. 7 shows another version of the disposable cell for the device of FIG. 5, which has a rectangular shape with plane-parallel walls forming the resonator cell. Here, the rectangular disposable cell 501' is supported between plane-parallel stirring transducers 510' and 511' incorporated into the grips 581 and 582.

Figure 9:
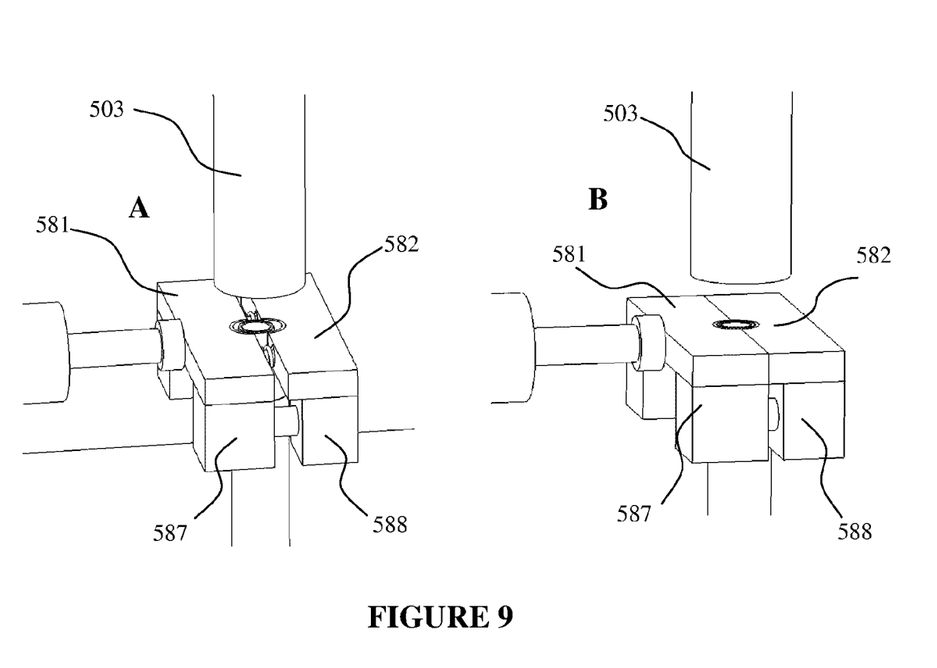
FIG. 9 shows the details of resonator cell loading of the device in FIG. 5: section A shows cell holder in the open position and section B shows the same in the closed position.

The grips can be opened in their "open" position by a two-part release relay as shown in more detail in FIG. 9. This figure shows a release portion 587 attached to the grip 581 and the release portion 588 attached to the grip 582. When an electrical release signal is supplied to the relay, the portions 587 and 588 move apart, therefore moving apart the grips 581 and 582 by overcoming the tension of the springs 583 and 584. This is shown on the left of FIG. 9 as an "open" position of the holder. Turning off the release signal brings the grips together by the forces of the tension of the extension springs 583 and 584 as illustrated on the right of FIG. 9 as the "closed" position of the holder.

FIG. 9 illustrates the first position of the cell assembly at the cell loading station 503. The release relay is activated and the disposable cell is dropped into the cell assembly. After that the release relay is deactivated and the grips are closed retaining the cell in place.

At the second position, the linear actuator moves the cell assembly under the liquid loading station as seen on FIG. 5 where the sample liquid is added to the cell. Appropriate microparticles may be already present in the cell or can be loaded into the cell at this or another station.

Figure 8:
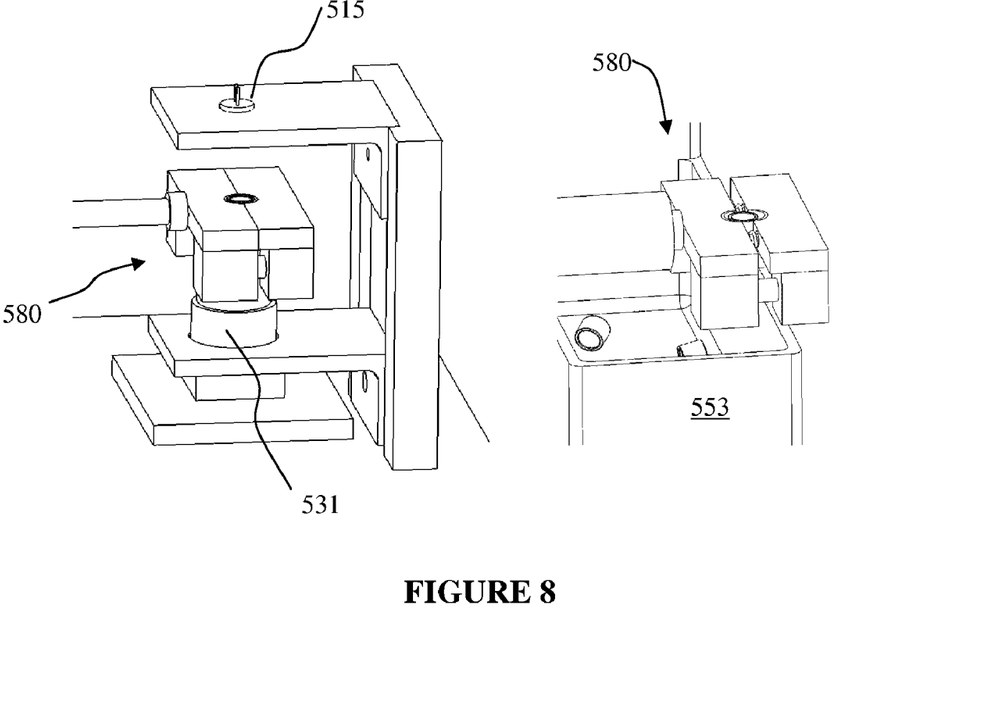
FIG. 8 illustrates the principle of operation of an embodiment depicted in FIG. 5, showing the device in the measuring position (on the left) and the exhaust position (on the right).

FIG. 8 illustrates the third position of the cell assembly 580 at the measuring station. Here the sample undergoes two phases of sonication to first form aggregates and then to disintegrate nonspecifically-bound aggregates and leave only the specifically-bound aggregates. Measurement of aggregates is also done at that station using the illumination source 515 such as an LED and the optical reading and measuring source 531 such as a digital camera. Measurement of aggregates can be advantageously accomplished by measuring one of several optical parameters including absorbance, optical reflectance, light scattering, and correlation spectroscopy parameters.

The fourth position where the disposable cell containing the sample is ejected into the disposal container 553 is not shown.

Figure 10:
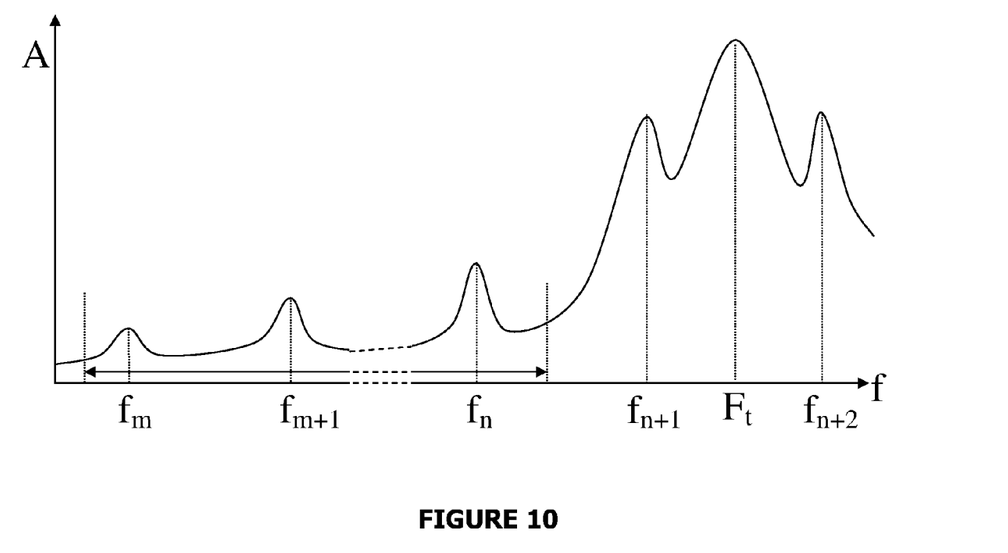
FIG. 10 shows amplitude/frequency dependence of ultrasonic resonator in the presence of standing waves in the liquid filling the resonator.

An important aspect of the method of the invention is the choice of parameters of ultrasonic transducers. Ideally, the swept-frequency mode of sonication requires a broadband source of ultrasound so that various successive resonance peaks of the liquid filled resonator have close energetic parameters. This requirement is in general difficult to satisfy since the common piezoceramic transducers are narrow band. Since the method of the invention does not need high levels of ultrasound intensity, similar to those needed to produce cavitational or thermal effects in various biomedical and industrial applications of ultrasound, it is possible to work in the frequency range, which is not too close to the resonance frequency of the transducer. FIG. 10 shows amplitude/frequency dependence of ultrasonic resonator in the presence of standing waves in the liquid filling the resonator. The horizontal bold arrow denotes such frequency region which is appropriate for swept-frequency mode of sample sonication according the method of current invention. The working frequency range should not include the resonance frequency and higher harmonics of the transducer. It is preferred to use broadband ultrasound transducers as a stirring transducer for the purposes of this invention.

Working at the frequencies far from the natural resonances of the transducer limits the levels of acoustic energy that can be generated in the sample. Therefore in certain applications, it might be necessary to take measures helping to get more energy from the transducer such as providing special acoustic matching layer bonded onto the surface of the transducer and optimal matching the output parameters of the driving electronic circuit with the electromechanical parameters of the transducer.

EXAMPLES

Three examples of detection of different analytes using ultrasound-assisted particle agglutination test according to the present invention are now presented. These examples illustrate the application of the methods of the invention to the tests based on the use of microbeads of different origin. Abbreviation UPA is used below in the text and in FIGS. 11 through 14 to denote Ultrasound-assisted Particle Agglutination procedures.

Example 1

Ultrasound-Assisted Particle Agglutination Method for Detection of HIV Antibody

Materials and Methods. Capillus HIV-1/HIV-2 test kits were obtained from Trinity Biotech. The Trinity Biotech Capillus HIV-1/HIV-2 kit (cat #6048G) is a qualitative latex agglutination test for the detection of antibodies to HIV-1/HIV-2 in human whole blood, serum or plasma. In this kit, the positive control is inactivated human serum or plasma containing antibodies to HIV-1 and HIV-2 whereas the negative control is normal human serum or plasma non-reactive for antibodies to HIV-1/HIV-2. These reagents are model systems and mimic real clinical samples: positive and negative human sera.

The Capillus HIV-1/HIV-2 is intended as an initial screening test in low volume testing facilities, in emergency situations and in areas where sophisticated equipment is not available. In addition, the test can be used as a supplemental assay in test algorithms.

Conventional agglutination procedure. The assay is performed on a capillary slide that consists of area for mixing of reagents, capillary flow channel and a viewing window. Positive control serum (lot # N 25818) was diluted 2-, 4-, 8-, 16 and 32-times with normal human male AB serum (Sigma, cat #H4522). The latex reagent (120 μl volume) and test sample (10 μl volume) are mixed in the mixing well on the slide. The mixed reagents are drawn to the flow channel and the reagents begin to flow by capillary action towards the viewing window. Flowing through the capillary channel takes approximately 15 minutes. The reaction is read visually when the latex solution reaches the viewing window. A smooth milky white appearance is considered as a non-reactive result.

UPA procedure. The positive control serum was double diluted with normal human serum (negative control) and the reagent mixture was prepared as described above by mixing 12 μl of latex beads and 1 μl of HIV positive serum. Then 4 μl of the reaction was transferred to a resonator cell of the UPA laboratory instrument, and exposed to an ultrasonic standing wave for 2 minutes. Then, the second phase of swept-frequency sonication was automatically applied for 1.5 min to disintegrate nonspecifically-bound aggregates. During this step, the image analysis software was used to quantitatively assess the agglutination. The final results are presented as an Aggregation Factor (AF).

Figure 11:
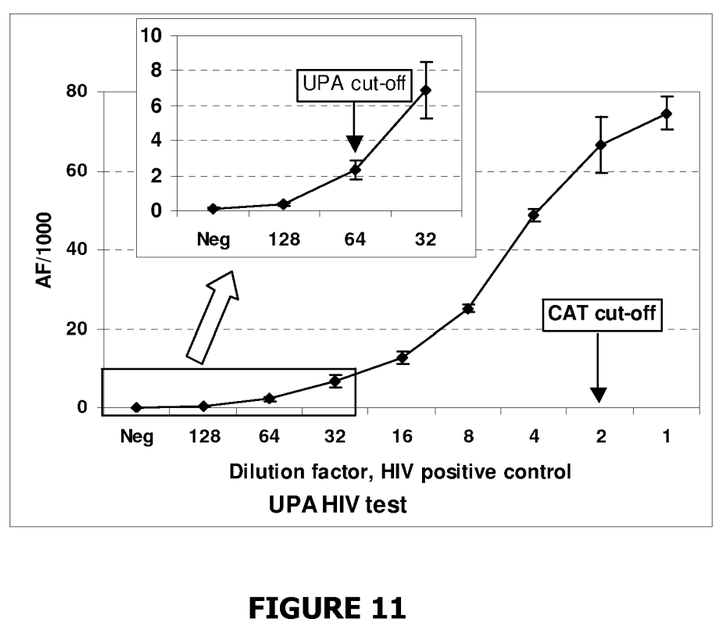
FIG. 11 shows the calibration curve for detection of HIV antibody. Insert in the graph is a zoom of data at high dilutions of the positive control. In the graph, the detection limit for conventional agglutination test (CAT) and UPA (ultrasound-assisted particle agglutination) test are also indicated.

Results. The analytical sensitivity of Capillus HIV test is limited by 1:2 dilution of positive control. The results obtained using UPA are shown in FIG. 11. For the sake of clarity, data is shown as obtained at high dilutions of the positive control in the insert of the graph. The detection limit (analytical sensitivity) of the method can be estimated as a double value of the background. As seen in FIG. 11, the assay performance for HIV detection is improved significantly. The analytical sensitivity of the optimized UPA method in this example is approximately 1:128 dilution of positive control serum.

It is should be noted that conventional particle agglutination test is highly qualitative and subjective, and, therefore, its sensitivity can be evaluated only approximately. The use of UPA methods on the other hand allows increasing the sensitivity of HIV antibody detection approximately 60-fold as compared to the conventional particle agglutination assay.

Example 2

Ultrasound-Assisted Particle Agglutination Method for Detection of Food-Borne Pathogenic Bacteria *E. coli* O157:H7 and *L. monocytogenes*

The procedure for detection of *E. coli* O157:H7 and *L. monocytogenes* requires a non-specific enrichment step, and it is desirable to conduct rapid tests using undiluted growth media samples. Therefore, in these experiments, the serum was inoculated with live bacteria, and after enrichment of bacteria in serum and broth, dilutions of the bacteria in the same broth that was used in second enrichment step were prepared. These procedures are described below in greater detail.

Materials and Methods. The *E. coli* O157:H7 and *L. monocytogenes* strains used in this study were obtained from International Collections (NCTC, ATCC). For *E. coli* samples, 10 μl of stock culture of *E. coli* O157:H7 was inoculated in 5 ml of Fetal Bovine Serum and incubated in autoclaved Erlenmeyer flask on orbital shaker at 37° C. at a speed of 200 rpm. After 15 hours of incubation, 20 μl of inocula were added to 100 ml of Luria Bertani (LB) Broth and incubated under the same conditions. Optical density at 600 nm of LB culture after 4 hr incubation was measured against sterile LB. For *Listeria* samples, the procedure was similar to that for *E. coli*, except the enrichment step was performed in Brain Heart Infusion broth (BHI, Difco, Detroit, Mich.) at 30° C.

For UPA, since second enrichment step was performed in LB broth for *E. coli* and in BHI broth for *Listeria*, samples were diluted in the same corresponding broths to mimic conditions for conducting experiments in clinical practice for detection of *E. coli* O157:H7 and *Listeria* in blood samples. Colony forming units (CFU) in each serially diluted sample were determined by plating procedure on LB or BHI agar medium for *E. coli* or *Listeria* samples, respectively. After plating, samples were inactivated by heat treatment at 70° C. for 15 min. Inactivated samples were also plated on agar to make sure that heat treatment killed bacteria. Prepared samples were stored at 4° C. before further analysis.

Figure 12:
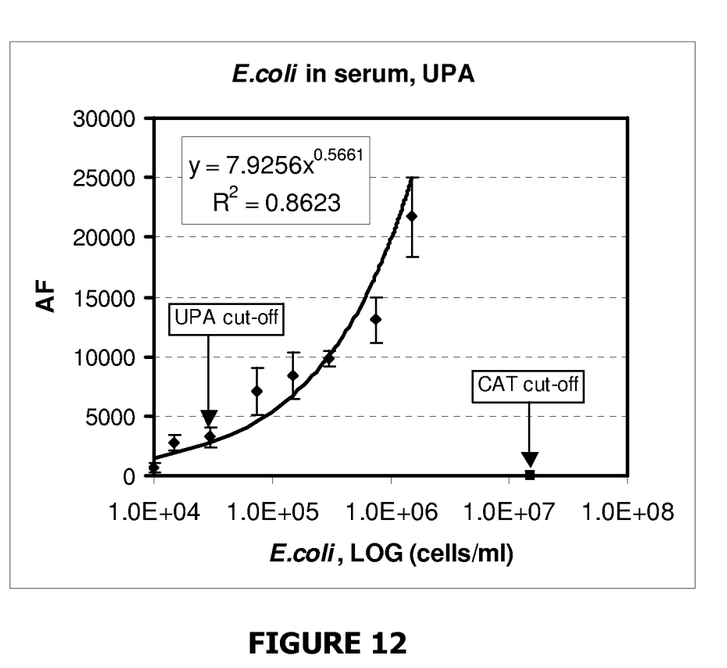
FIG. 12 shows the ultrasound-assisted particle agglutination test calibration curve for detection of *E. coli* O157:H7 in serum.

Results. 1) *E. coli* detection. CAT experiments, performed using samples prepared as described above, showed that the CAT detection limit (analytical sensitivity) is approximately $1.5 \times 10^7$ cells/ml. The UPA calibration curve obtained using LB broth for detection of *E. coli* O157:H7 in blood samples is shown in FIG. 12. The results presented here show that the UPA allows the detection of bacteria in growth media used for sample enrichment. Using an accurate regression analysis for the calibration curve presented in FIG. 12, the UPA detection limit was calculated to be $3.0 \times 10^4$ cells/ml. Thus, one the UPA sensitivity for detection of *E. coli* O157:H7 is approximately 500-fold higher than that for CAT.

2) *Listeria* detection. The sensitivity of CAT test for *Listeria* detection is approximately $2.4 \times 10^9$ cells/ml. The UPA results obtained for *Listeria* positive control (Microgen kit) diluted in BHI broth and enriched sera *Listeria* samples are shown in FIG. 13.

Figure 13:
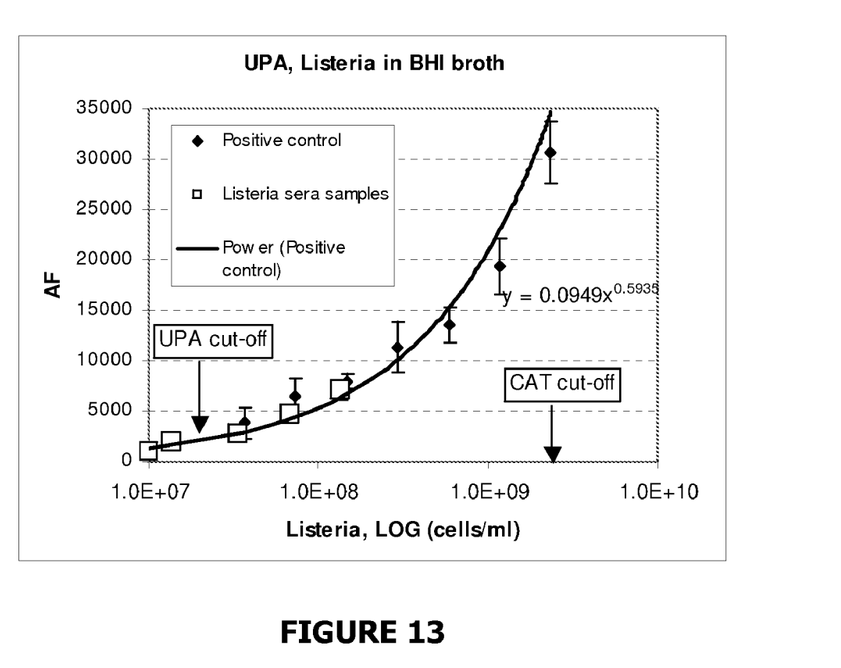
FIG. 13 shows ultrasound-assisted particle agglutination test calibration curves prepared using positive control and sera samples for detection of *Listeria* in BHI broth.

As can be noted on FIG. 13, the calibration curves obtained for the positive control and sera samples practically coincide. The sensitivity of the UPA calculated using regression analysis is $1.93 \times 10^7$ cells/ml. Thus, UPA detection limit is approximately 120-fold lower than that for CAT.

Example 3

Increasing of the Sensitivity of Haemagglutination Assays by Ultrasound-Assisted Particle Agglutination Procedure Serum or reverse grouping test is used as adjunct to cell grouping (forward blood typing) for detection of anti-A and anti-B antibodies in serum or plasma. Serum grouping (reverse blood typing) by conventional haemagglutination test (CHT) and UPA methods was performed as follows.

Tube Test Method. Test serum was 2×, 4×, 8× and 16× diluted with non-reactive serum AB. 70 μl of serum was mixed with 1 drop of Reagent Red blood cells in each Pyrex glass tube (Sigma cat 3 CLS980010-72E). The reagent mixture was incubated at room temperature for 30 minutes (room temperature incubation for a prolonged time is recommended to enhance the sensitivity of the method). Then, cells were spun down at 1000×g for 15 sec. The pellet was examined after gentle resuspension of cells. Positive reaction is characterized as clear liquid with red pellet on the bottom of test tube whereas negative reaction is characterised by no agglutination. Serum obtained from blood of the donor of blood group B (serum B) was mixed with red blood cells $A_1$, and serum AB was used as a negative control (Serum AB contains neither anti-A nor anti-B).

UPA method. Ultrasound-assisted particle agglutination assay was performed as described above for tube tests, that is, 70 μl of test serum was mixed with 1 drop of reagent red blood cells. After incubation of solutions in glass tubes for 30 minutes at room temperature, 4 μl of the solution was transferred to a resonator cell of the UPA laboratory instrument, and exposed to ultrasonic field 21 MHz for 10 seconds during the first phase of sonication. Then, the second phase of sonication (frequency range is between 2,000 to 32,000 kHz) was automatically turned on for 1.5 min to disintegrate nonspecifically-bound aggregates. At the same time, the image analysis software was applied to quantitatively assess the agglutination. The final results are presented as Aggregation Factor (AF).

Figure 14:
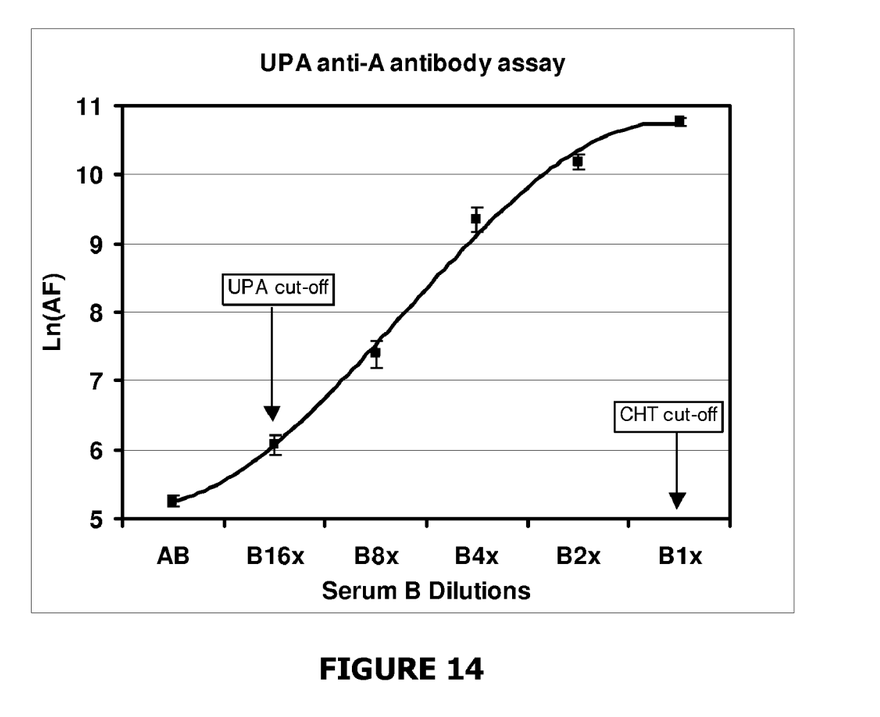
FIG. 14 shows the calibration curve for detection of anti-A antibodies in serum B using ultrasound-assisted particle agglutination test (blood group testing of serum B): plot of ln (AF) vs. Serum B dilutions.

Results. Results show that only in tube 1 in which undiluted serum B was mixed with red cells $A_1$, positive agglutination reaction occurs. In all other tubes, in which diluted serum B and undiluted serum AB were used, no agglutination occurs. The detection limit of the tube test method can be defined as a serum B maximal dilution at which agglutination is detected by visual inspection of the solution. Thus, the detection limit of tube test method is undiluted serum B. The results obtained using UPA are shown in FIG. 14. As can be seen here, the sensitivity of the UPA method is 1:16 serum B dilution. Thus, the use of UPA allows increasing the sensitivity of anti-A antibody detection 16-fold as compared to a conventional haemagglutination assay.

Although the invention herein has been described with respect to particular embodiments, it is understood that these embodiments are merely illustrative of the principles and applications of the present invention. For example, in addition to antigen-antibody interactions used to describe the main principles of the invention, it is also advantageously applicable to cell receptor-ligand interactions, nucleic acid-nucleic-acid, protein-nucleic acid interactions and ligand/nucleic acid—protein interactions. In general, the invention is applicable to a broad spectrum of applications where the microparticles are covered with a specific binding agent designed to detect the presence of a particular analyte. It is therefore to be understood that these and other numerous modifications may be made to the illustrative embodiments and that other arrangements may be devised without departing from the spirit and scope of the present invention as defined by the appended claims.

What is claimed is:

1. An ultrasound-assisted particle agglutination method to detect presence of an analyte in a liquid contained in a resonator cell with an ultrasound transducer acoustically coupled thereto, said resonator cell further containing a plurality of microparticles, each of said microparticles covered with a binding agent with high affinity to said analyte, said method comprising a first phase of exposing said liquid to an ultrasound field at a resonance frequency of said liquid in said cell, said resonance frequency identified by analyzing the electrical impedance of said ultrasound transducer, said exposure causing formation of a nodal pattern and migration of said microparticles to the locations of said nodal pattern creating clusters of said microparticles; said first phase further characterized by formation of specifically- and nonspecifically-bound aggregates of said microparticles in said clusters; said method including a second phase of stirring said liquid with a swept-frequency sonication by varying a driving signal frequency of said transducer in a range from a predefined minimum frequency to a predefined maximum frequency, said predefined minimum and maximum frequencies are selected to include therebetween at least two resonance frequencies of said liquid in said resonator cell as detected by analyzing the electrical impedance of said ultrasound transducer, said stirring causing said nonspecifically-bound aggregates to disintegrate; said method including a third phase of optical or acoustical detection of microparticles aggregates indicating the presence of said analyte in said liquid.

2. The method as in claim 1, wherein said first phase is achieved by providing a driving signal to said transducer at a frequency corresponding to a resonance frequency of said liquid in said resonator cell for a period of time sufficient to form said specifically-bound aggregates of said microparticles.

3. The method as in claim 1, wherein said first and said second phases are achieved by applying said swept-frequency sonication to said liquid, said varying of said driving signal frequency in said range including applying at least one said resonance frequency for a period of time sufficient to form said specifically-bound aggregates of said microparticles.

4. The method as in claim 1, wherein said microparticles are selected from a group consisting of biological cells, proteins, latex beads microparticles, glass microparticles, silica microparticles, and microparticles made from clay minerals.

5. The method as in claim 1, wherein said analyte is selected from a group consisting of a protein, a DNA, an RNA, virus, bacteria, ligand and a physiologically active substance.

6. The method as in claim 1, wherein said frequency of said driving signal is in a range from about 1 MHz to about 50 MHz.

7. An ultrasound-assisted particle agglutination assay apparatus to detect presence of an analyte in a liquid, said apparatus comprising:
a resonator cell containing therein said liquid and a plurality of microparticles, each of said microparticles covered with a binding agent with high affinity to said analyte;
a stiffing ultrasound transducer acoustically coupled to said resonator cell; and
a control system including a microprocessor adapted to detect a resonance frequency of said liquid in said resonator cell by analyzing electrical impedance of said stiffing ultrasound transducer and to drive said stirring transducer at said resonance frequency during formation of specifically- and nonspecifically-bound aggregates of said microparticles; said microprocessor further adapted to drive said stirring transducer in a swept-frequency mode of sonication for stirring of said liquid and disintegration of said nonspecifically-bound aggregates by varying a frequency of a driving signal of said transducer in a range from a predefined minimum frequency to a predefined maximum frequency, said predefined minimum and maximum frequencies are selected to include therebetween at least two resonance frequencies of said liquid in said cell as detected by said control system using said electrical impedance of said stirring ultrasound transducer.

8. The apparatus as in claim 7 further including aggregate detection means.

9. The apparatus as in claim 7, wherein said stirring transducer is a broadband ultrasound transducer, said control system further including a voltage control oscillator adapted to send a driving signal to said stirring transducer through a complex resistor, said oscillator controlled by said microprocessor defining the driving signal frequency of said stiffing transducer, said control system further including an amplitude or phase detector adapted to receive the driving signal from said complex resistor and further adapted to provide a feedback signal to said microprocessor indicating changes in electrical impedance of said stiffing transducer in vicinity of said resonance frequencies.

10. The apparatus as in claim 9 further including a measuring ultrasound transducer and a pulse-echo electronic system adapted to drive said measuring transducer to send and receive short ultrasonic pulses, whereby said measuring transducer and said pulse-echo electronic system are adapted to measure backscattering properties of said liquid and therefore comprise said aggregate detection means.

11. The apparatus as in claim 10, wherein said measuring transducer is driven at a frequency in a range from about 50 MHz to about 150 MHz.

12. The apparatus as in claim 7, wherein said apparatus including a plane-parallel stirring transducer adapted to serve as both a reflector and a receiver of ultrasound and located opposite said stirring transducer, said control system including a broadband amplifier, a phase-locked loop chip, and a bandpass filter.

13. The apparatus as in claim 12, wherein said microprocessor is adapted to switch said driving signal frequency of said transducer from one resonance frequency to another by inverting a phase of said phase-locked loop chip.

14. The apparatus as in claim 8, wherein said aggregate detection means are optical means including an illumination source and a light detection source thereof, said optical means adapted to detect optical properties of said liquid in the resonator cell.

15. The apparatus of claim 14 wherein said detecting of optical properties comprises measurement of an optical parameter selected from a list consisting of absorbance, optical reflectance, light scattering, and correlation spectroscopy parameters.

16. The apparatus as in claim 13, wherein said resonator cell incorporating a transparent bottom, said apparatus further including a resonator cell assembly for holding said resonator cell, said assembly is supported by and moved to an appropriate position by a moving means.

17. The apparatus as in claim 16, wherein said moving means is a linear actuator.

18. The apparatus as in claim 16, wherein said resonator cell assembly includes a holder comprising a first grip with said stiffing transducer attached thereto and a second grip with said plane-parallel transducer attached thereto, said grips and said transducers adapted to retain said resonator cell between and in close contact with said transducers in a "closed" position of said grip, said holder adapted to release said resonator cell from said grips in an "open" position thereof.

19. The apparatus as in claim 18, wherein said resonator cell is a disposable cylindrical cartridge, said stirring and plane-parallel stiffing transducers are shaped as segments of a tube with their internal radii being equal to the external radius of said cartridge.

20. The apparatus as in claim 18, wherein said resonator cell is a disposable rectangular cartridge, said stirring and plane-parallel stirring transducers are flat and positioned at a certain distance so as to retain the parallel sides of said cartridge therebetween.

21. The apparatus as in claim 18, wherein said holder further includes two extension springs attached to said grips and adapted to bring said grips together in a "closed" position.

22. The apparatus as in claim 21, wherein said holder further including an electrical release relay attached to said grips and adapted to move them apart in said "open" position of said holder when activated by an electrical signal from said control system.

23. The apparatus as in claim 17, wherein said linear actuator is adapted to move said resonator cell assembly starting from a first position at a cartridge loading station to a second position at a liquid loading station, followed by a move to a third position at a measuring station, and finally to a fourth position to a discarding station.

* * * * *